United States Patent [19]

Mausner

[11] 4,140,759
[45] Feb. 20, 1979

[54] PROTEIN SHAMPOO

[75] Inventor: Jack J. Mausner, East Hills, N.Y.

[73] Assignee: Helena Rubinstein, Inc., New York, N.Y.

[21] Appl. No.: 815,305

[22] Filed: Jul. 13, 1977

[51] Int. Cl.² ............................................. A61K 7/06
[52] U.S. Cl. ................................. 424/70; 252/89 R; 252/545; 252/546; 252/547; 424/359
[58] Field of Search .................... 424/70, 359; 252/89, 252/545, 546, 547

[56] References Cited

U.S. PATENT DOCUMENTS

| 3,932,610 | 1/1976 | Rudy et al. | 424/70 |
| 3,934,003 | 1/1976 | Tuma et al. | 424/70 |
| 3,950,417 | 4/1976 | Verdicchio et al. | 424/70 |
| 3,954,725 | 5/1976 | Johnsen et al. | 424/70 |
| 3,957,971 | 5/1976 | Oleniacz | 424/70 |
| 3,959,460 | 5/1976 | Vanlergerghe et al. | 424/70 |
| 3,962,418 | 6/1976 | Birkofer | 424/70 |
| 3,980,768 | 9/1976 | White | 424/70 |
| 3,990,991 | 11/1976 | Gerstein | 424/70 |
| 3,997,659 | 12/1976 | Knohl et al. | 424/70 |
| 3,998,761 | 12/1976 | Gary et al. | 424/70 |
| 4,009,256 | 2/1977 | Nowak, Jr. et al. | 424/70 |
| 4,047,888 | 9/1977 | Papantoniou | 424/70 |

OTHER PUBLICATIONS

Schimmel Briefs No. 358, 1/1965, Schimmel & Co. Inc., Newburgh, N.Y.

Primary Examiner—Allen J. Robinson
Attorney, Agent, or Firm—Burgess, Ryan and Wayne

[57] ABSTRACT

A liquid shampoo containing a biologically derived protein detergent having unusual mildness to the hair and scalp and also having hair conditioning properties.

16 Claims, 5 Drawing Figures

LIPO PROTEIN NATURAL DETERGENT COMPLEX
U.V. SPECTRUM

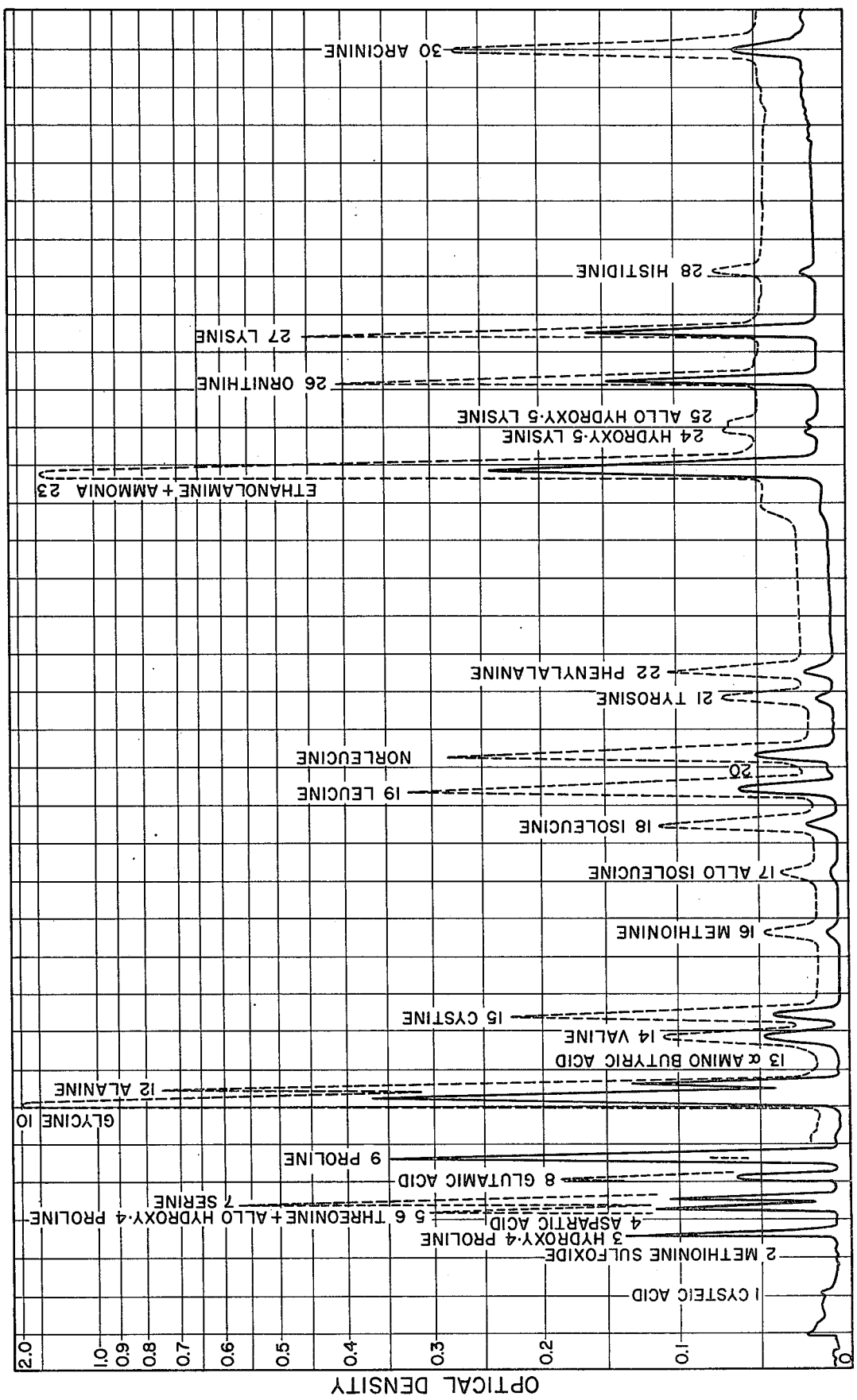

PROTEIN SHAMPOO

BACKGROUND OF THE INVENTION

The present invention relates to shampoos and, more particularly, the present invention relates to a shampoo composition containing a special protein detergent of biological origin.

Cosmetics for the treatment of hair are applied topically to the scalp and hair. While they can never be used for therapeutic purposes, they must be harmless to the skin and scalp, to the hair, and to the mucous membranes and should not have any toxic effect, general or local, in normal conditions of their use. This would appear to be a simple matter but the tissues are living organs which could react differently to the application of foreign substances.

Types of hair are generally divided into three groups. The first is normal hair, the second is dry hair, and the third is oily hair. In the case of dry hair, the scalp and the hair show a decrease of hydrophilic lipids. This condition can be artificially corrected due to the great variety of raw materials available. It has been established, however, that in order to achieve efficiency, specific biological substances must be used.

The lubrication of scalp hair and the maintenance of suppleness are to a great extent due to sebum that secures the protection of hair against mechanical erosion, dehydration, attack by bacteria, and oxidation by sunlight. The sebum also secures the connection between corneal cells of the scalp and the cuticular scales of the hair.

SUMMARY OF THE INVENTION

It is, therefore, a primary object of the present invention to provide a shampoo composition which cleans the hair and scalp without doing any damage to the fragile biological equilibrium of the scalp and hair.

It is another object of the present invention to provide a shampoo composition based on a biologically derived protein detergent which is uniquely mild and possesses hair conditioning properties.

It is a further object of the present invention to provide a shampoo composition based on a biologically derived protein detergent which possesses anti-bacterial properties.

Consistent with the foregoing objects, a shampoo composition is provided which is based on a biologically derived protein detergent known as a lipo protein natural detergent complex which is a complex mixture of lecithins, phospholipids, lipo-protein, lipo-oligopeptides, and amino acids. The shampoo also contains conventional ingredients such as anionic surfactants, boosters, stabilizers, preservatives, colorings, fragrances, and the like. Additionally, it is within the purview of the present invention to include in the shampoo composition other optional ingredients which are recognized as being conventional in the art for such preparations. These include, for example, organic or inorganic acids for pH adjustment, preservatives, antioxidants, chelating agents and the like.

The surfactant system comprises one or more water-soluble surface-active agents, i.e., an anionic, nonionic, or amphoteric surfactant, or a mixture thereof, which produces acceptable foam or whose foam is supplemented by a suds improver. Preferred anionic detergents are sulfonated and sulfated anionic detergents and in particular the sodium, magnesium, ammonium, mono- di- and triethanolamine salts of sulfated fatty alcohols as well as these salts of the sulfonated alkylaryl compounds, all of which have a total of from 12 to 21 carbon atoms. Typical anionic detergents include sodium lauryl sulfate, sodium oleyl succinate, ammonium lauryl sulfosuccinate, sodium lauryl ether sulfate, ammonium lauryl sulfate, monoethanolamine lauryl sulfate, triethanolamine lauryl sulfate, sodium dodecylbenzene sulfonate, triethanolamine dodecylbenzene sulfonate and sodium N-lauroyl sarcosinate. Other anionic detergents include soaps such as triethanolamine lauratemyristate and triethanolamine oleate.

Nonionic detergents include fatty acid alkanolamides and the alkylene oxide (ethylene oxide and propylene oxide) condensates of a hydrophobic base such as a long chain fatty alcohol or an alkylphenol. Typical of the fatty acid alkanolamides are those having a total of from 10 to 21 carbon atoms, such as lauric diethanolamide, coconut oil monoethanolamide and lauric isopropanolamide. The alkylene oxide condensates of long chain fatty alcohols include $C_{10}$ to $C_{21}$ fatty alcohols condensed with 3 to 20 moles of ethylene oxide, such as the ethylene oxide condensates of lauryl alcohol, myristyl alcohol and palmityl alcohol. The alkylene oxide condensates of alkylphenols include the alkylphenols having a $C_8$ to $C_{15}$ alkyl group condensed with 3 to 20 moles of ethylene oxide, such as the octylphenol-8 mole ethylene oxide condensate, the nonyl phenol-10 mole ethylene oxide condensate and the dodecyl phenol-10 mole ethylene oxide condensate.

Amphoteric or ampholytic detergents include N-lauryl-N'-carboxymethyl-N'-(2-hydroxyethyl) ethylenediamine, coco-beta-alanine, and the Miranol compounds described in U.S. Pat. Nos. 2,528,378 and 2,781,354.

Other examples, well known to the art, may be found in the literature such as "Surface Active Agents" by Schwartz and Perry and "Surface Active Agents and Detergents" by Schwartz, Perry and Berch, both Interscience Publishers, New York, N.Y., the disclosures of which are incorporated herein.

The most preferred detergents are the anionics such as the lauryl sulfates, particularly ammonium lauryl sulfate. Sodium lauryl sulfate and sodium lauryl ether sulfate are also very suitable for use in the compositions of the invention.

Optionally, the detergent system may also contain from about 0.2 to about 15 weight percent, based on the weight of the total composition, of one or more lather boosters and/or stabilizers to increase sudsing power and foam stability. Examples of these would include coco amide, lauric diethanolamide, lauric isopropanol amide, coconut monoethanol amide, betaines, sulfobetaines, coco dimethylamine oxide, coco bis 2-hydroxyethyl amide oxide. The most preferred booster is the reaction product of 2 moles of diethanolamine with 1 mole of coconut fatty acids sold under the trademark of "Schercomid CDOR Extra". The most preferred stabilizer is myristyl dimethylamine oxide which is sold under the trademark "Ammonyx MO".

Another ingredient of the composition is a thickener. The preferred thickener would be one which not only thickens the solution but also acts as a conditioner and gives a clear solution. It has been found that the high molecular weight fatty acid mono- or di- ester of a high molecular weight polyethylene glycol is preferred. Thus, the thickener-conditioner would be a mono- or di- ester of polyethylene glycol 6000 with a higher fatty acid having from about 6 to about 33 carbon atoms.

Exemplary of such acids are caproic acid, heptoic acid, caprylic acid, pelargonic acid, capric acid, undecylic acid, lauric acid, tridecylic acid, myristic acid, pentadecylic acid, palmitic acid, margaric acid, stearic acid, nondecylic acid, arachidic acid, eicosane-carboxylic acid-(1), behenic acid, lignoceric acid, cerotic acid, melissic acid, psyllastearic acid.

The preferred esters are the dilaurate, the dipalmitate, and the distearate of polyethylene glycol 6000. The most preferred thickener-conditioner is polyethylene glycol 6000 distearate. The thickener-conditioner is present in a range of about 0.5 to about 5% by weight of the total composition.

DESCRIPTION OF THE PREFERRED EMBODIMENTS

The critical ingredient of the shampoo composition of the present invention is the lipo-protein natural detergent complex which is produced by Laboratoires Serobiologiques S. A. of Nancy, France, and sold under the name "CLP-3". CLP-3 is a detergent of biological origin in a hydro-polyol excipient. The protein complex is a combination of hydrophilic lipid complexes normally present in the tissues and lipo-protein detergent complexes. It is a mixture of lecithins, phospholipids, lipo-protein, and lipo-oligopeptides. The excipient is glycerine. Basically, CLP-3 is a 50% by weight solution of the lipo-protein natural detergent complex in glycerine and water, the glycerine content being about 5% by weight.

The lipo-protein natural detergent complex is a biologically derived material having the following properties:

| | |
|---|---|
| Viscosity | 2.45 poises |
| pH at 10% | 6.00 |
| Saponification Index | 12 |
| Acid Index | 2 |
| Proteins | 0.65 % |
| Total lipoproteins | 3.00 % |
| U.V. spectograph | FIG. 1 |
| I.R. spectograph | FIG. 2 |
| Electrophoresis of the lipoproteins | FIG. 3 |
| Thin layer chromatograph | FIG. 4 |
| Column chromatograph | FIG. 5 |

FIG. 1 is the ultraviolet spectograph of the complex as measured in a 1% aqueous solution. The scan was 0.5 nm/sec. The chart had 25 nm/inch and the span was 1.0.

Figure 4:
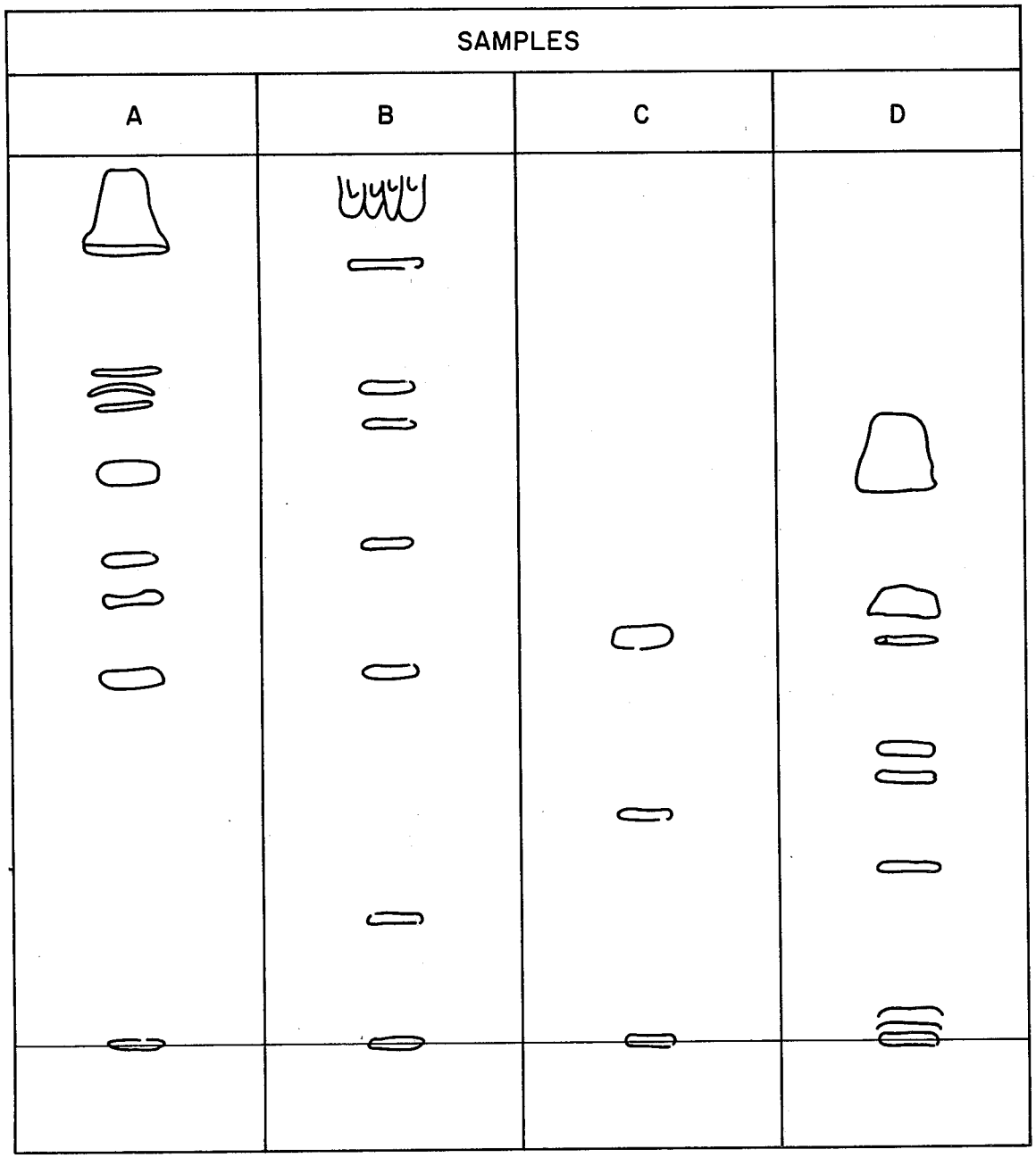

FIG. 4 shows the thin layer chromatograph of the complex. The support was silica gel 254366 on a type 60 glass plate, 20 × 20 (300 μm thick). Samples A, B, and D were extracted with acetone-alcohol-chloroform. Sample C was extracted with alcohol-acetone-alcohol-chloroform. 20 μl of the samples were deposited over 1 cm, at 2 cm. from the lower edge. The solvent for samples A and B was a chloroform, methanol, water (65/25/4) system. The solvent for samples C and D was a petroleum ether, ethyl ether, acetic acid (85/15/2) system. Development was 16 cm. from the deposit. The reading for samples A and C was under ultraviolet radiation at 254 nm. Samples B and D were treated with a 5% phosphomolybdic acid solution in methanol and dried for 10 minutes at 100° C.

FIG. 5 is a characterization of the lipoamino acids in the complex by column gas chromatography.

The amount of CLP-3 used in the shampoo composition of the present invention can range from about 5 to about 30% by weight of the total composition. The additional surfactant as described above could be present in an amount of from about 10 to about 50% by weight of the total composition.

The invention will be better understood by reference to the following example which is considered to be illustrative and not in any way limiting:

EXAMPLE

A shampoo composition according to the present invention was made utilizing the following ingredients:

| | Percent by weight |
|---|---|
| PHASE A | |
| Deionized Water | 38.60 |
| Sequestrene Na2[1] | 0.20 |
| Germall 115[2] | 0.35 |
| Methyl Paraben | 0.10 |
| Ammonyx MO | 0.50 |
| Standapol A[3] | 30.00 |
| CLP-3 | 20.00 |
| PHASE B | |
| Polyethylene Glycol 6000 Distearate | 1.50 |
| PHASE C | |
| Citric Acid (20% aq. soln., wt/wt) | 3.25 |
| PHASE D | |
| Schercomid CDOR Extra | 5.00 |
| Perfume THTC[4] | 0.50 |
| | 100.00% |

[1] ethylenediaminetetraacetic acid disodium salt
[2] imidazolidinyl urea
[3] ammonium lauryl sulfate
[4] a rose, jasmin, muguet complex enhanced by a green, aldehyde note rounded out with a musk vetiver background. This product is manufactured and sold by Polak's Frutal Works, Inc., Middletown, New York, U.S.A.

The ingredients of Phase A were placed in a vessel and heated with agitation to 55° C. until clear and uniform. The PEG 6000 distearate of Phase B was melted in a separate vessel with agitation. The temperature was about 65° C. When melted, Phase B was added to phase A with continuous agitation. When the batch was uniform it was cooled to about 35°-40° C. and Phase C was added with agitation.

In the meantime, Phase D was mixed in another container until perfectly clear. Phase D was then added to the already mixed phases A, B and C at about 35°-40° C. before the batch reached its maximum viscosity. After Phase D was thoroughly blended into the batch, it was cooled to about 25° C. with slow agitation.

It was already mentioned that CLP-3 has extraordinary antibacterial properties. Studies were conducted on this aspect of the material. As controls, several hairs which had not been washed for a week were taken from various male and female adults, grown on nutrient agar poured into Petri dishes and placed on a steam bath at 33° C. for 48 hours. The organisms recovered were identified following the usual techniques and were identified in every case. It was noteworthy that 95% of the samples contained cocci gram positive (staphylococcus, micrococcus), 19% had bacilli gram positive (corynebacterium bacillus), 9% had various yeasts (including 50% identified as pityrosporum ovale), and 5% each of bacilli gram negative and aspergilaceae. 32% of the samples observed had two types of contamination and 3% of the samples observed had three types of contamination. It is also noteworthy that the growth of the organisms, such as staphylococcus since this is most prevalent, is not abundant on the hair under normal conditions because of the pH (about 5) and bacteriostatic effect of some scalp secretions. But, their presence is highly frequent as shown by the foregoing figures.

A piece of contaminated agar on which staphylococcus was cultured as already described, was removed from the original Petri dish and set on the metal support of a scanning electron microscope and pictures taken. A thin coat of agar was poured on the support of a scanning electron microscope and a suspension of staphylococcus was incubated on it. Pictures were then taken. The pictures of the known culture were compared with the pictures of the culture grown from the hair and indicated that the organisms were the same. Scanning electron microphotographs were also made of pieces of hair showing the organisms on the hair. Hair was subjected to the action of a staphylococcus suspension and then photographed under the scanning electron microscope, showing the damage done.

Two commercial shampoos were compared with a shampoo made from CLP-3 in the pure and diluted form (1/12 in sterile distilled water). In each case, a Petri dish was prepared by pouring 0.5 ml. of a suspension containing 2 billion organisms per milliliter of staphylococcus collected from bacterial infected hair, and 10 ml. of liquified agar into the dish with slow shaking to homogenize. Just before solidification, 1 ml. of the product to be tested was added on the surface of the plate. The culture was incubated for 48 hours at 33° C. and a reading was taken. The results are shown in the following Table where the two commercial shampoos are denoted as 1 and 2, respectively and the CLP-3 is denoted as Sample 3.

TABLE I

| Dish N° | Dishes after 48 h. in steam stove at + 33° C. | | | | | |
|---|---|---|---|---|---|---|
| | 1 | 2 | 3 | 1 D | 2 D | 3 D |
| Shampoo | pure BJOH | pure DOP | pure CLP-3 | diluted BJOH | diluted DOP | diluted CLP3 |
| Bacteriological & bactericidal activity | none | very weak | excellent | very weak | weak | excellent |

An analysis was made of the constituents of sebum, the outer layer of the scalp, and the hair before shampooing. A similar analysis was made after shampooing with a shampoo composition containing CLP-3. The results of these analyses are shown in Table II.

It will be apparent that the objects set forth at the outset have been successfully achieved. While this invention has been described by reference to present preferred embodiments, they are to be considered as exemplary and not in any way limiting. The invention is limited only by the scope of the appended claims.

TABLE II

| CONSTITUENTS | SEBUM | OUTER LAYER OF THE SCALP | HAIR | SHAMPOO WITH CLP-3 |
|---|---|---|---|---|
| Fatty Acid | + | | + | |
| Fatty acid esters | + | | + | + |
| Glycerides | +++ | ++ | | |
| Mixed hydrocarbons | ++ | | | |
| Waxes | + | + | + | |
| Sterols | + | + | + | |
| Squalene, Squalene | + | | | |
| Phospholipids | | + | | + |
| Lecithins | | + | | + |
| Lipo Proteins | | | | |
| Globulins | | + | | + |
| Albumins | | + | | + |
| Keratine (amino acids) | | | | |
| Lysine | + | + | + | + |
| Histidine | + | + | + | + |
| Arginine | + | + | + | + |
| Aspartic acid | + | + | + | + |
| Threonine | + | + | + | + |
| Serine | + | + | + | + |
| Glutamic acid | + | + | + | + |
| Proline | + | + | + | + |
| Glycine | + | + | + | + |
| Alanine | + | + | + | |
| ½ Cystine | + | + | | |
| Valine | + | + | + | + |
| Methionine | + | + | + | + |
| Isoleucine | + | + | + | + |
| Leucine | + | + | + | + |
| Tyrosine | + | + | + | + |
| Phenylalanine | + | + | + | + |

Figure 1:
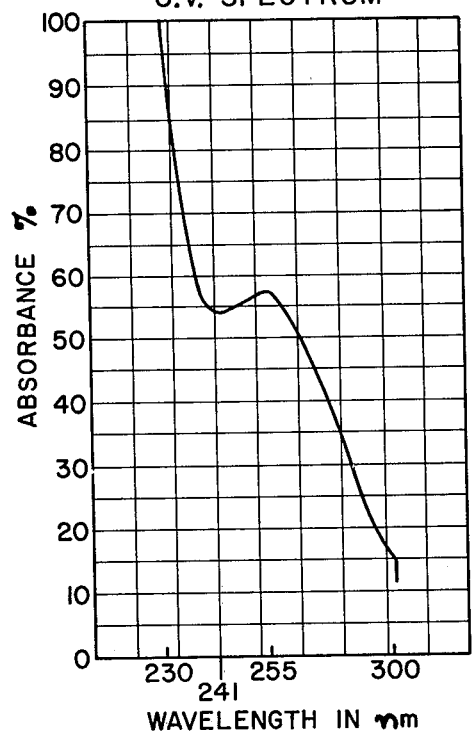
Figure 3:
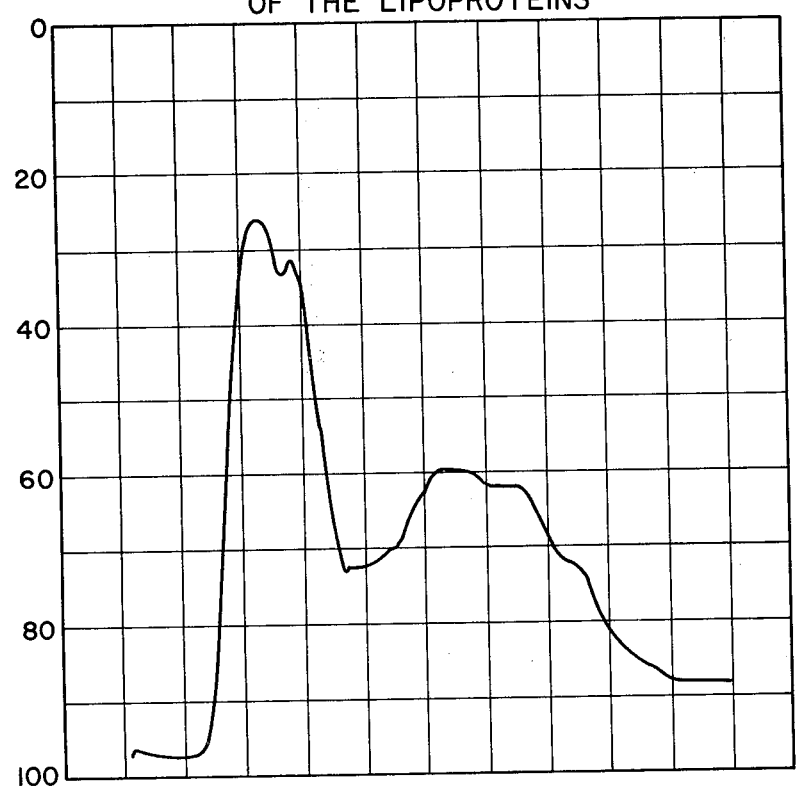
FIG. 3 is the electrophoresis curve of the complex.
Figure 2:
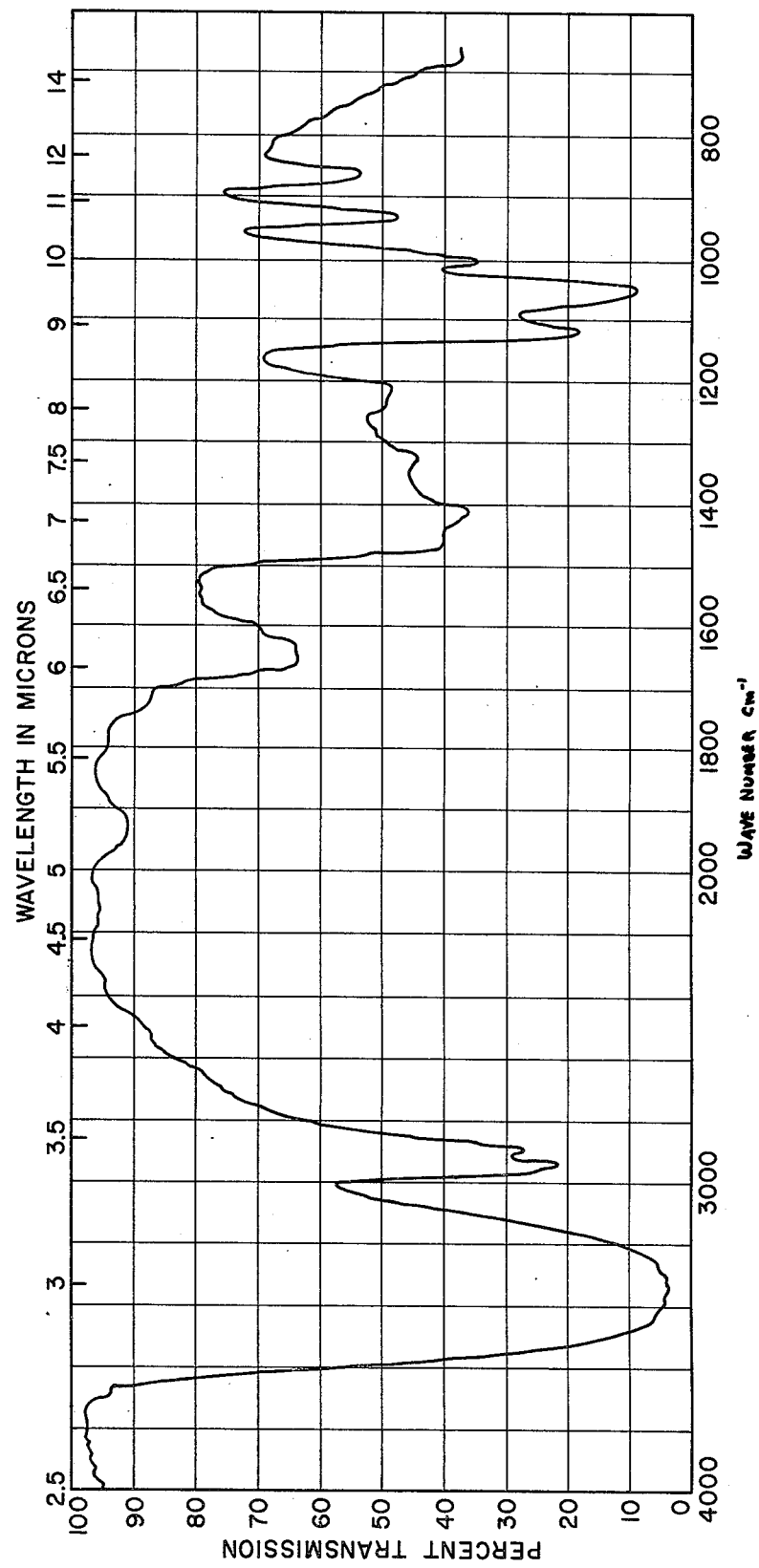
FIG. 2 is the infrared spectrum of the complex.

What is claimed is:

1. A hair shampoo composition comprising an aqueous glycerin solution of an effective amount of lipoprotein natural detergent complex having a viscosity of 2.45 poises, a pH of 6.00, a saponification index of 12, an acid index of 2, total proteins 0.65%, total lipoproteins 3.00, and characterized by the ultraviolet spectrograph shown in FIG. 1, the infra-red spectrograph shown in FIG. 2, the electrophoresis curve shown in FIG. 3, the thin layer chromatogram shown in FIG. 4, and the column chromatogram shown in FIG. 5.

2. The composition as claimed in claim 1, further comprising an effective amount of an anionic, nonionic or amphoteric surfactant, an effective amount of a foam booster, and an effective amount of a foam stabilizer.

3. The composition as claimed in claim 2, wherein said surfactant is an anionic surfactant.

4. The composition as claimed in claim 3, wherein said surfactant is an alkyl sulfate.

5. The composition as claimed in claim 4, wherein said surfactant is ammonium lauryl sulfate.

6. The composition as claimed in claim 2, wherein said booster is an alkanolamide.

7. The composition as claimed in claim 6, wherein said booster is the reaction product of two moles of diethanolamine with one mole of coconut fatty acids.

8. The composition as claimed in claim 2, wherein said stabilizer is an amine oxide.

9. The composition as claimed in claim 8, wherrein said stabilizer is myristyl dimethylamine oxide.

10. The composition as claimed in claim 2, further comprising an effective amount of means for thickening said solution and conditioning the hair.

11. The composition as claimed in claim 10, wherein said means is a higher fatty acid mono- or di- ester of a high molecular weight polyethylene glycol.

12. The composition as claimed in claim 11, wherein said fatty acid contains from 6 to 33 carbon atoms.

13. The composition as claimed in claim 12, wherein said means is polyethylene glycol 6000 distearate.

14. The composition as claimed in claim 2, further comprising a chelating agent, a preservative, and a perfume.

15. The composition as claimed in claim 1, comprising, in percent by weight:

| Ingredient | Amount |
| --- | --- |
| surfactant | 10–50 |
| lipo protein natural detergent complex | 5–30 |
| booster | 0.2–15 |
| stabilizer | |
| Thickener and hair conditioner | 0.5–3 |
| chelating agent | effective amount |
| Preservative | effective amount |

-continued

| Ingredient | Amount |
| --- | --- |
| water | qs. 100% |

16. The composition as claimed in claim 15, comprising, in percent by weight:

| Ingredient | Amount |
| --- | --- |
| ammonium lauryl sulfate | 30.00 |
| lipo protein natural/detergent detergent complex | 20.00 |
| reaction product of 2 moles diethanolamine with one mole cocounut fatty acids | 5.00 |
| myristyl dimethylamine oxide | 0.50 |
| polyethylene glycol 6000 distearate | 1.50 |
| disodium EDTA | 0.20 |
| citric acid - 20% aq. soln. | 3.25 |
| imidazolidinyl urea | 0.35 |
| methyl paraben | 0.10 |
| perfume | 0.50 |
| deionized water | 38.60 |

* * * * *

UNITED STATES PATENT OFFICE
CERTIFICATE OF CORRECTION

Patent No. 4,140,759         Dated February 20, 1979

Inventor(s) Jack J. Mausner

It is certified that error appears in the above-identified patent and that said Letters Patent are hereby corrected as shown below:

Column 2, line 5 : change "succinate" to --sulfosuccinate-- lines 11-12: change "lauratemyristate" to --laurate/myristate-- line 52: change "monoethanol amide" to --monoethanolamide--

Column 6, line 59: change "wherrein" to --wherein--

Column 8, line 12: change "lipo protein" to --lipo--

Signed and Sealed this

Thirtieth Day of October 1979

[SEAL]

Attest:

RUTH C. MASON
Attesting Officer

LUTRELLE F. PARKER
Acting Commissioner of Patents and Trademarks